United States Patent [19]
Kuenstner

[11] Patent Number: 5,692,503
[45] Date of Patent: Dec. 2, 1997

[54] METHOD FOR NONINVASIVE (IN-VIVO) TOTAL HEMOGLOBIN, OXYHEMOGOLOBIN, DEOXYHEMOGLOBIN, CARBOXYHEMOGLOBIN AND METHEMOGLOBIN CONCENTRATION DETERMINATION

[76] Inventor: J. Todd Kuenstner, 26 Wild Duck Rd., Wyckoff, N.J. 07481

[21] Appl. No.: 402,245

[22] Filed: Mar. 10, 1995

[51] Int. Cl.$^6$ ............................................. A61B 5/000
[52] U.S. Cl. ...................................... 128/633; 356/41
[58] Field of Search ............................. 128/633, 664–7; 356/39–41

[56] References Cited

U.S. PATENT DOCUMENTS

| | | | |
|---|---|---|---|
| 4,997,769 | 3/1991 | Lundsgaard | 356/39 |
| 5,183,042 | 2/1993 | Harjunmaa et al. | 128/633 |
| 5,337,745 | 8/1994 | Benaron | 128/664 |
| 5,377,674 | 1/1995 | Kuestner | 128/633 |

*Primary Examiner*—Jennifer Bahr
*Assistant Examiner*—Bryan K. Yarnell
*Attorney, Agent, or Firm*—Kilpatrick Stockton; Charles W. Calkins

[57] ABSTRACT

Non-invasive in-vivo and in-vitro methods for determining a person's total hemoglobin concentration as well as the concentration of the hemoglobin species which contribute to this total concentration, i.e., oxy-, deoxy-, carboxy-, and methemoglobin are described. The measurement comprises a ratio formed by dividing absorbance data at analyte wavelengths by absorbance data at reference wavelengths. In a first embodiment the analyte wavelengths occur at a local maximum of each of the hemoglobin species in the visible region. The reference wavelengths include those in the short wavelength near-infrared region from 800 to 1300 nm. In order to determine the concentration of each hemoglobin species a dA/A treatment is utilized comprising a difference term of absorbance data in the region from 800 to 1300 nm divided by the absorbance at a local maximum for each species. These measurements at local maxima are then combined in a series of simultaneous equations which are then solved for the concentration of each species and the total concentration. In a second embodiment, analyte wavelengths are selected in the range of 480 nm to 630 nm, with separate analyte wavelengths for each hemoglobin species. The measurements are then combined in a series of simultaneous equations which are then solved for the concentration of each species and the total concentration of hemoglobin. In addition, a measurement for total hemoglobin concentration which uses a ratio of absorbance at a triple isosbestic point and the above described difference term is described.

22 Claims, 4 Drawing Sheets

ABSORPTION SPECTRA
— HB (HEMOGLOBIN)
— — — HBO$_2$ (OXYHEMOGLOBIN)
+++++ HBCO (CARBOXYHEMOGLOBIN)
- - - - - HI (METHEMOGLOBIN)
— — — (SULFHEMOGLOBIN)

METHOD FOR NONINVASIVE (IN-VIVO) TOTAL HEMOGLOBIN, OXYHEMOGOLOBIN, DEOXYHEMOGLOBIN, CARBOXYHEMOGLOBIN AND METHEMOGLOBIN CONCENTRATION DETERMINATION

FIELD OF THE INVENTION

The present invention relates to a non-invasive (in-vivo) and in-vitro method for determining hemoglobin concentration and for determining the concentration of the various hemoglobin species.

BACKGROUND

The use of absorbance data at multiple wavelengths combined in ratio form and the use of derivative absorbance ratios for non-invasive measurements of hemoglobin was first described in my U.S. Pat. No. 5,377,674, the disclosure of which is hereby incorporated by reference. As set forth in U.S. Pat. No. 5,377,674, hemoglobin concentration may be accurately measured non-invasively (in-vivo), and in whole blood (in-vitro), using many regions of the visible and near-infrared spectrum and many different data treatments. The data treatments which were presented included derivative data treatments which do not require a path-length or scattering measurement and therefore could be readily used with a device modeled on the pulse oximeter to obtain measurements at the peak and trough of blood pulsation. The use of absorbance data at multiple wavelengths combined in ratio form and the use of derivative absorbance ratios for non-invasive measurements of hemoglobin was first described in U.S. Pat. No. 5,377,674.

Other investigators have shown the feasibility of transcutaneous measurement of hematocrit using a simple absorbance ratio of absorbance at 805 nm divided by absorbance at 1310 nm. See, R. R. Steuer, D. Harris and J. M. Conis, *American Clinical Laboratory*, June 1992, pp. 18–21 and W.O. Patent 94/23643 filed Apr. 12, 1993 by R. R. Steuer and D. Harris.

In my research, spectra of 70 whole blood samples were analyzed using the visible and short-wavelength near-infrared regions. The whole blood samples comprised venous blood samples and were analyzed using a model 6500 NIRSystems spectrophotometer. A simple ratio of absorbance at 824 nm divided by absorbance at 1216 mm yielded a correlation coefficient of 0.964 and a standard error of calibration of 0.784 gm/dL when compared to a standard laboratory measurement of hemoglobin concentration.

Adding a third wavelength and using an A/dA data treatment improved the accuracy further. The A/dA treatment comprises an ordinary absorbance term, A divided by a difference term, dA where:

A=ordinary absorbance at a wavelength dA=the difference in absorbance between two wavelengths.

In the art, dA is also referred to as the first derivative with a particular gap, wherein the gap refers to the spacing between the two wavelengths.

When a third wavelength was added, specifically, 592 nm, and the data treatment was absorbance at 592 nm divided by the difference in absorbance at 820 nm and at 1180 nm, the prediction error was reduced to 0.586 grams/dL from 0.784 grams/dl.

Alternatively, a third wavelength consisting of 596 nm could be added and the data treatment could consist of the difference term, dA, between absorbance at 810 nm and 1288 nm divided by the ordinary absorbance, A, at 596 nm. This treatment is the dA/A treatment. In this case, the dA/A treatment would yield a prediction error of 0.471 gm/dL. The absorbance at 592 and the absorbance at 596 nm occur near an isosbestic point of oxyhemoglobin and deoxyhemoglobin. The isosbestic point is at 586 nm.

When a dA term consisting of the difference in absorbance at 1280 nm and 1380 nm was used instead of a difference in absorbance at 810 nm and 1288 nm the accuracy deteriorated so that the correlation coefficient of the prediction set was 0.59.

The high correlation obtained using an A term at 596 nm suggests the possibility of using several wavelengths in this region for the determination of the separate hemoglobin species in addition to the total hemoglobin concentration.

The above data set obtained on venous blood samples using a model 6500 NIRSystems spectrophotometer, while useful for the region from 590 nm and above may not be optimal for the region below 590 nm. However, in this part of the electromagnetic spectrum, the spectrophotometry of hemoglobin and its species has been extensively investigated and characterized. The wealth of information available in this region and the fact that several commercially available instruments use this region for whole blood, reagent-free hemoglobin determinations suggested that these measurements could be adapted to a non-invasive setting. This adaptation would offer improved accuracy of the total hemoglobin determination and separate determinations of the various hemoglobin species.

SUMMARY OF THE INVENTION

The present invention results from my discovery that it possible to measure the various species of hemoglobin, in addition to total hemoglobin concentration, through the use of spectrophotometric measurements in the visible and the short- wavelength near-infrared region and ratios of a derivative absorbance term and an ordinary absorbance term. These ratios are then used in a series of simultaneous equations in a manner which will be readily understood by those of ordinary skill in the art. The advantages of using this part of the electromagnetic spectrum include that light sources, such as LED's, suitable for use in hand-held instruments for the spectrophotometric measurements are currently available and the possibility of measuring the various species of hemoglobin in addition to the total hemoglobin concentration. It should be noted that, for measuring total hemoglobin concentration alone, the longer wavelength near-infrared region may prove more accurate.

The Corning Co-Oximeter 2500 measures total hemoglobin, oxyhemoglobin, deoxyhemoglobin, carboxyhemoglobin, methemoglobin and sulfhemoglobin using a multiple wavelength technique whereby the wavelengths occur at local maxima for each of the hemoglobin species. The method makes measurements at 500, 569, 577, 620 and 760 nm, uses five simultaneous equations and requires ultrasonic cell lysis and a path-length measurement. This method has been well characterized by A. Zwart and coworkers (A. Zwart, A. Buursma, E. J. van Kampen and W. G. Zjilstra, *Clinical Chemistry*, 30/3, 1984, pp. 373–379.)

The Instrumentation Laboratories 282 CO-Oximeter measures total hemoglobin concentration, oxy-, deoxy-, carboxy- and methemoglobin using lysed whole blood, a path-length measurement and a set of simultaneous equations. However, the measurements are made at 535.0, 585.2, 594.5 and 626.6 nm which are not necessarily local maxima for each of the hemoglobin species.

I have discovered that the systems of measurement described above may be adapted for non-invasive measurements and could be useful for in-vitro measurements which would not require a path-length measurement or cell lysis.

DETAILED DESCRIPTION OF THE INVENTION

Figure 1:
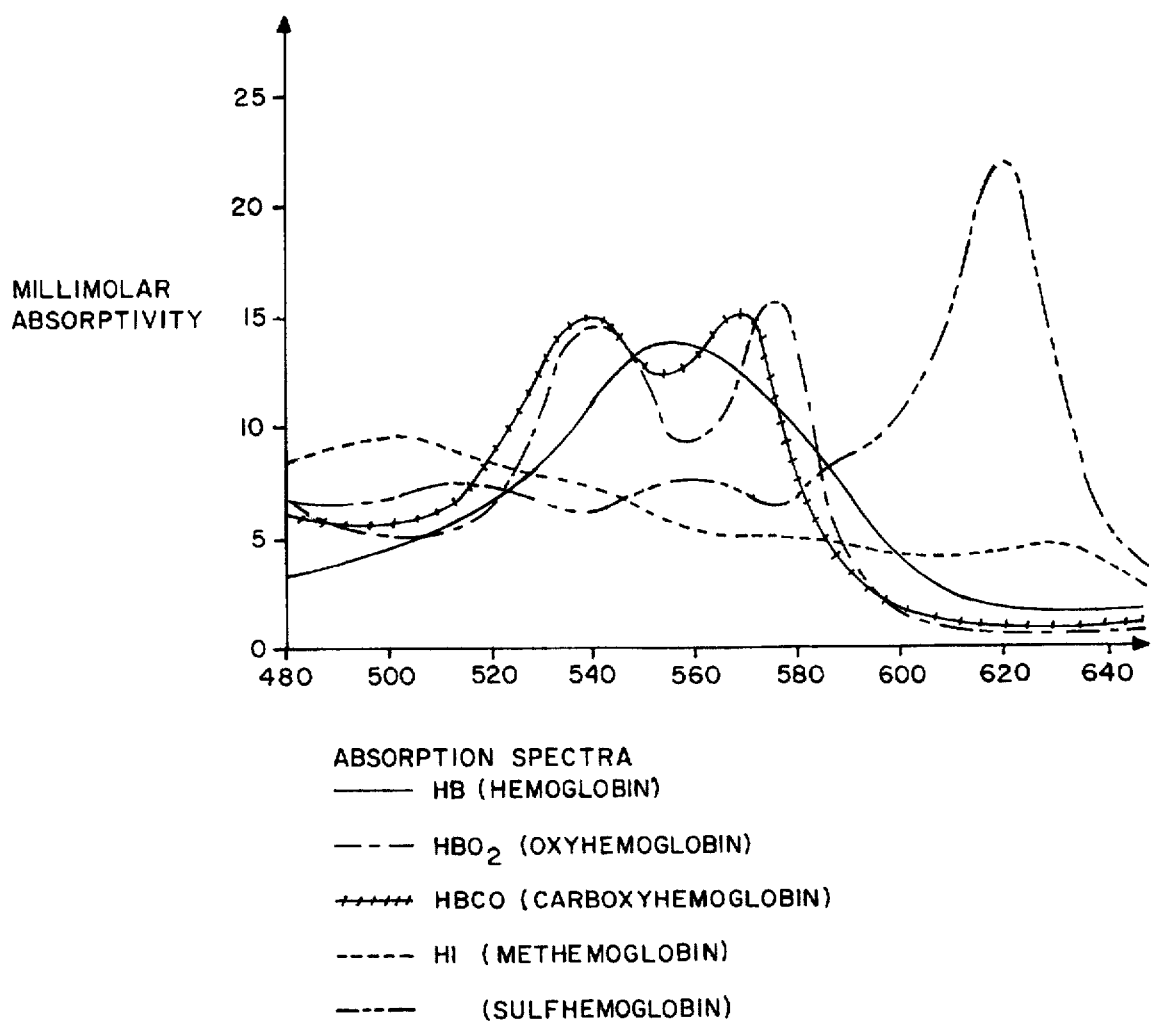
FIG. 1-show exemplary spectra of hemoglobin species including oxyhemoglobin, deoxyhemoglobin, carboxyhemoglobin, methemoglobin, and sulfhemoglobin in the visible region.

The method of the present invention for determining, in-vivo, the concentration of one or more hemoglobin species comprises:

generating an absorbance data measurement by
measuring the absorbance of light at a plurality of wavelengths in capillary bed tissue said plurality of wavelengths including:
at least one analyte wavelength for a hemoglobin species;
a first reference wavelength; and
a second reference wavelength;
and comparing the absorbance data measurement to reference data generated by a correlation study to determine the concentration of the hemoglobin species of the tissue.

The comparison of the absorbance data measurement to the reference data is advantageously performed by the dA/A treatment described above and in more detail below, wherein:

dA=the difference in absorbance between the first and second reference wavelengths, and A is the ordinary absorbance at the analyte wavelength. The comparison may also be performed by an A/dA treatment.

The method of the present invention may be utilized to determine the concentration of more than one hemoglobin species from a single set of absorbance data, by measuring the absorbance at additional analyte wavelengths corresponding to additional hemoglobin species. In an embodiment of the method of the present invention where absorbance data for additional analyte wavelengths is generated, concentration of the individual hemoglobin species may be determined by comparing the results of a multivariate analysis such as the one described below to reference data generated in a correlation study.

The method of the present invention may be utilized to measure the concentration of known hemoglobin species including oxyhemoglobin, deoxyhemoglobin, carboxyhemoglobin, methemoglobin, and sulfhemoglobin as well as total hemoglobin concentration.

In a first embodiment of the in-vivo method of the present invention the concentration of each species is measured through the use of at least one analyte wavelength corresponding to a local substantial maximum absorbance of the species. The concentration of total hemoglobin may be determined by determining the concentration of each hemoglobin species and then summing the concentrations of each hemoglobin species to obtain the total hemoglobin concentration.

Local maxima absorbance of the various hemoglobin species in the visible region, suitable for use in this embodiment of the method of the present invention include the following:

| Hemoglobin Species | Local Maxima Absorbance |
|---|---|
| oxyhemoglobin | 577 nm |
| deoxyhemoglobin | 760 nm |
| carboxyhemoglobin | 569 nm |
| methemoglobin | 500 nm |
| sulfhemoglobin | 620 nm |

Suitable reference wavelengths for use in the method of the present invention include those in the short-wavelength near-infrared region from 800 nm to 1300 nm. Preferably, the first and second reference wavelengths are separated by at least 300 nm.

In the first embodiment of the method of the present invention the absorbance due to arterial blood may be isolated by performing a first set of measurements at the peak of a blood pulsation through the tissue, and a second set of measurements at the trough of a blood pulsation through the tissue, and using the difference between the first and second set of measurements.

In a second embodiment of the in-vivo method of the present invention, the concentration of known hemoglobin species including oxyhemoglobin, deoxyhemoglobin, carboxyhemoglobin, methemoglobin, and sulfhemoglobin may be determined through the solution of a set of N equations with N unknowns where each unknown is a concentration of a particular hemoglobin species. The total number of hemoglobin species whose concentration is to be determined equals N.

The first equation in the set of N equations is generated by:

measuring the absorbance of light at a plurality of wavelengths including a first analyte wavelength; a first reference wavelength; and a second reference wavelength.

The second equation in the set of N equations is generated by measuring the absorbance of light at a plurality of wavelengths including a second analyte wavelength and the first and second reference wavelengths. The third equation in the set of N equations is generated by measuring the absorbance of light at a plurality of wavelengths including a third analyte wavelength and the first and second reference wavelengths. Additional equations in the set of N equations may be generated in the same fashion.

The preferred wavelengths to utilize for the first, second, third, fourth etc. analyte wavelengths include those between 450 and 950 nm. In this second embodiment of the method of the present invention the analyte wavelengths chosen do not have to correspond to any particular point on the absorbance curve for the species being analyzed.

Preferred wavelengths to utilize for the first and second reference wavelengths include those between 800 and 1300 nm. Preferably, the first and second reference wavelengths are separated by at least 300 nm.

In this second embodiment of the method of the present invention the absorbance due to arterial blood may be isolated by performing a first set of measurements at the peak of a blood pulsation through the tissue, and a second set of measurements at the trough of a blood pulsation through the tissue, and using the difference between the first and second set of measurements.

Other embodiments of the present invention are also possible.

The method of the present invention may be advantageously performed by modifying commercially available spectrophotometric equipment such as the CIBA-Corning 2500 CO-Oximeter and the Instrumentation Laboratories 282 CO-Oximeter methods described above so that these methods do not require a path length measurement or cell lysis. This modification would be suitable for in-vitro measurements.

Zwart and coworkers described the method used in the CIBA-Corning 2500 CO-Oximeter. As shown by A. Zwart, once the spectral absorptivity curves of the hemoglobin species are known, a mixture of any number of them can be analyzed by multicomponent analysis. The simplest approach is to measure the absorbance of the mixture at as many wavelengths as there are components likely to be present. This yields n equations of the type $$A_{\lambda,n} = e_1 c_1 l + e_n c_n l$$

where $A_{\lambda,n}$ is the absorbance at wavelength lambda n, $e_n$ is the millimolar absorptivity of component n at wavelength lambda n, $c_n$ is the concentration of component n and l is the light-path length. Using absorbance data at five different wavelengths, the concentration of five species of hemoglobin may be determined.

In the non-invasive setting or in the case when cell lysis is not employed, a path-length determination is difficult if not impossible to perform using existing technology. The absorbance at each of the above five wavelengths will be affected by changes in scattering and path-length unless some normalization factor is employed. As described under the background section, a preferred normalization factor for this region is a dA term consisting of a difference in absorbance between 800 nm and 1300 nm.

If each of the above five equations is divided by the normalization factor, in this case the difference 815 nm and 1288 nm, each will have the form shown below:

$$A_{\lambda,n}/(A_{815}-A_{1288}) = (e_1 c_1 l + e_n c_n l)/(e_{oxyHgb}{}^e THgb^{1-s}w + Hgb^c w + Hgb^b)$$

where: oxyHgb=oxyHemoglobin
THgb=total Hemoglobin
w=water
Hgb=Hemoglobin.

For any given measurement, the path-length is the same so that l divides out. In the denominator, the difference in absorbance between 815 nm and 1288 nm in blood samples is essentially the difference in absorbance at 815 nm which is primarily due to oxy- and deoxyhemoglobin and the absorbance at 1288 nm which is primarily due to water with a smaller contribution from Hemoglobin in the blood. The difference in absorbance between 815 nm and 1288 nm for a blood sample, while not strictly constant from individual to individual, varies proportionately less than the absorbance at either single wavelength, i.e., 815 nm or 1288 nm. As an approximation, this difference term may be treated as a constant term and thus ignored since all terms are divided by the same constant term. The above equations then become:

$$A_{80\,n}/(A_{815}-A_{1233}) = e_1 c_1 + e_2 c_2 + + e_n c_n$$

Alternatively, the wavelengths employed by the Instrumentation Laboratories CO-Oximeter, 535.0, 585.2, 594.5, and 626.6 nm could be used with the same type of normalization treatment described above using a dA term of a difference between 815 nm and 1288 nm and a series of simultaneous equations which may be solved for the concentrations of the unknowns which consist of oxy-, deoxy-, carboxy- and methemoglobin.

If one used 2 analyte wavelengths with the dA term (a total of 4 wavelengths), a simple system for measuring the total hemoglobin would be achieved and one could measure the concentration of dyshemoglobins.

For example, using absorbance data from 586 nm which is an isosbestic point for oxy- ($HbO_2$) and deoxyhemoglobin (Hb) and from 522 nm which is an isosbestic point for carboxy- and methemoglobin, one could obtain the concentration of total hemoglobin, "functional" hemoglobins (oxy- and deoxyhemoglobin) and dyshemoglobins (carboxy- (HbCO) and methemoglobin (Hi)). The following set of simultaneous equations could be solved for the 2 unknowns, $(C_{HbO2}+C_{Hb})$ and $(C_{HbCO}+C_{Hi})$, which are functional hemoglobins and dyshemoglobins, respectively.

$$A_{586} = e(C_{HbO2}+C_{Hb}) + e(C_{HbCO}+C_{Hi})$$

$$A_{522} = e(C_{HbO2}+C_{Hb}) + e(C_{HbCO}+C_{Hi})$$

Alternatively, one could use two different wavelengths to solve for the total hemoglobin, the concentration of oxy-, deoxy- and carboxyhemoglobin and the concentration of methemoglobin using the following equations.

$$A_{548} = e(C_{HbO2}+C_{HB}+C_{HbCO}) + eC_{Hi}$$

$$A_{506.5} = e(C_{HbO2}+C_{Hb}+C_{HbCO}) + eC_{Hi}$$

In addition to measuring hemoglobin concentration noninvasivley, the above described multiple wavelength method would likely improve the accuracy of the current pulse oximeter which uses a ratio of absorbance at 660 nm divided by the absorbance at either 910 or 940 nm. Yelderman and New reported a correlation coefficient of 0.98 when the current pulse oximeter was compared to the reference method. However, correlation curves for the pulse oximeter with CO-Oximeter references show considerable non-linearity in the pulse oximeter measurement. Current pulse oximeters are known to be quite inaccurate when levels of deoxyhemoglobin are high. Use of A/dA terms, as disclosed herein, would probably improve the accuracy of current oximeters which use a simple ratio of the absorbances at each wavelength.

An even simpler measurement which employs fewer wavelengths solely for the purpose of hemoglobin concentration measurement, is a ratio formed by dividing the absorbance at 548 nm by a difference between absorbance at 815 nm and 1288 nm. It is possible that this simple approach will be inaccurate when there are significant quantities of methemoglobin present. At 548 nm, there is a triple isosbestic point for oxy-, deoxy- and carboxyhemoglobin. At this point these species have an extinction coefficient of 12.40, while methemoglobin has an extinction coefficient of only approximately 5.40.

The method of the present invention may advantageously be utilized in-vivo as a non-invasive method for deterraiding the concentration of hemoglobin species in the blood. The present invention also includes methods for the in-vitro determination of one or more hemoglobin spades in a blood sample comprising:

generating an absorbance dam measurement by
measuring the absorbance of light at a plurality of
wavelengths in the blood sample including:
at least one analyte wavelength;

a first reference wavelength; and a second reference wavelength;

and comparing the absorbance data measurement to reference data generated by a correlation study to determine the concentration of the hemoglobin species in the blood sample.

The comparison of the absorbance data measurement to the reference data is advantageously performed by the dA/A or A/dA treatment described above, wherein:

dA=the difference in absorbance between the first and second reference wavelengths, and A is the ordinary absorbance at the analyte wavelength.

The in-vitro method of the present invention may be utilized to determine the concentration of more than one hemoglobin species from a single set of absorbance data, by measuring the absorbance at additional analyte wavelengths corresponding to additional hemoglobin species. In an embodiment of the method of the present invention where absorbance data for additional analyte wavelengths is generated, the concentration of the individual hemoglobin species may be determined by comparing the results of a multivariate analysis, such as the one described above, to reference data generated in a correlation study.

The in-vitro method of the present invention may be utilized to measure the concentration of known hemoglobin species including oxyhemoglobin, deoxyhemoglobin, carboxyhemoglobin, methemoglobin, and sulfhemoglobin, and total hemoglobin concentration. The in-vitro method of the present invention includes first and second embodiments similar to those described above with reference to the in-vivo method of the present invention.

In a first embodiment of the in-vitro method of the present invention, the concentration of each hemoglobin species is measured individually, through the use of at least one analyte wavelength corresponding to a local substantial maximum absorbance of the species. The concentration of each hemoglobin species may be determined in the manner described above with reference to a first embodiment of the in-vivo method of the present invention. The concentration of total hemoglobin may be determined by determining the concentration of each hemoglobin species and then summing the concentrations of each hemoglobin species to obtain the total hemoglobin concentration.

Local maxima absorbance of the various hemoglobin species in the visible region, and reference wavelengths, suitable for use in the in-vitro method of the present invention include those listed in the table above.

In a second embodiment of the in-vitro method of the present invention the concentration of known hemoglobin species including oxyhemoglobin, deoxyhemoglobin, carboxyhemoglobin, methemoglobin, and sulfhemoglobin may be determined through the solution of a set of N equations with N unknowns where each unknown is a concentration of a particular hemoglobin species. The total number of hemoglobin species whose concentration is to be determined equals N. The generation and solution of these equations may be performed in the manner described above with reference to a second embodiment of the in-vivo method of the present invention.

The present invention may be further understood with reference to the attached figures.

FIG. 1 shows the absorbance spectra of the various hemoglobin species in the visible region. Inspection of these spectra shows local maxima for oxy-, deoxy-, carboxy-, met- and sulfhemoglobin at 577, 760, 569, 500, and 620 nm respectively. In addition, a triple isosbestic point for oxy-, deoxy-, and carboxyhemoglobin is apparent at 548 nm. At this point, the absorbance of methemoglobin is substantially less than that of the other species.

Figure 2:
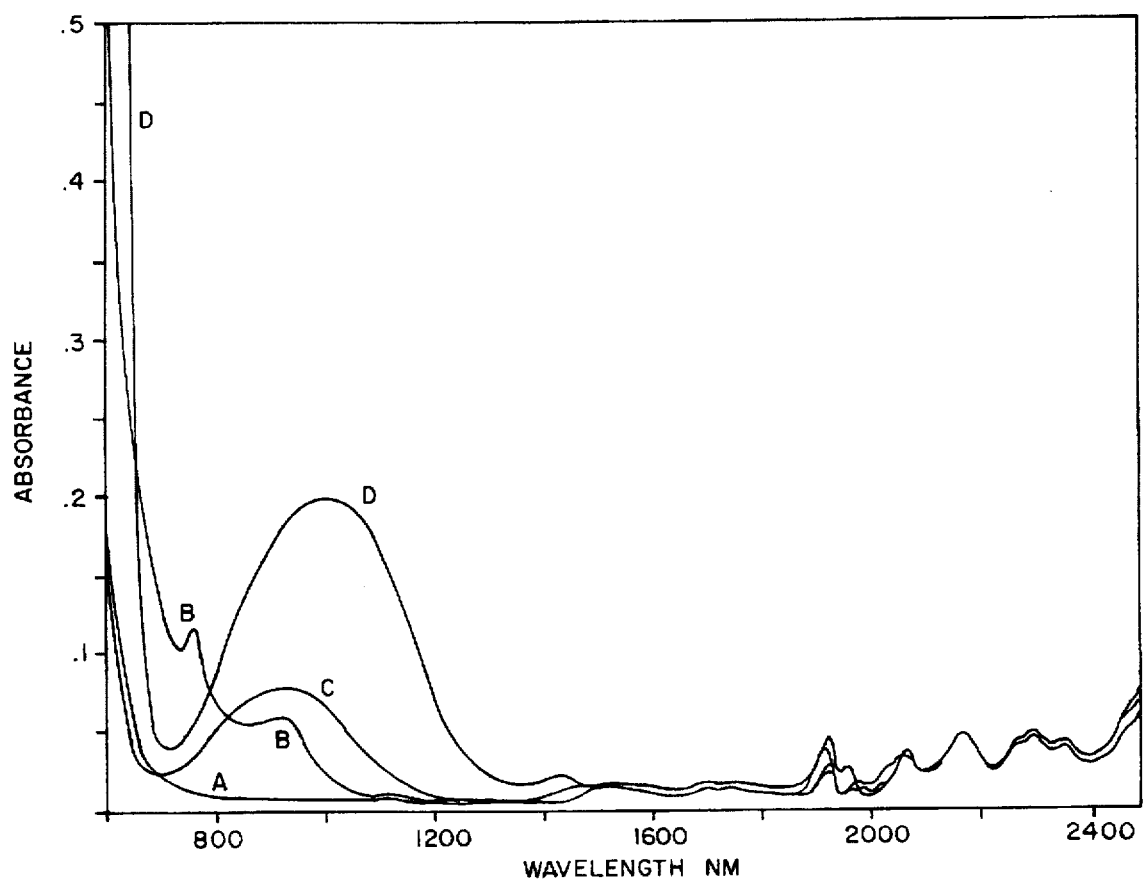
FIG. 2 shows the absorbance spectra of the hemoglobin species in the near-infrared region.

FIG. 2 shows the absorbance spectra of the various hemoglobin species in the region from 600 to 2400 nm. A is carboxy-, B is deoxy-, C is oxy- and D is methemoglobin. The species were produced using standard methods reported in the literature, and spectral subtraction was employed to remove the absorbance due to water. The spectra show that the absorbance of the hemoglobin species in the region from 1200 to 1300 nm is very similar for each species (with the exception of methemoglobin) and that the absorbance for each species in the above region is much lower than its absorbance in the visible region at 600 nm.

Figure 3:
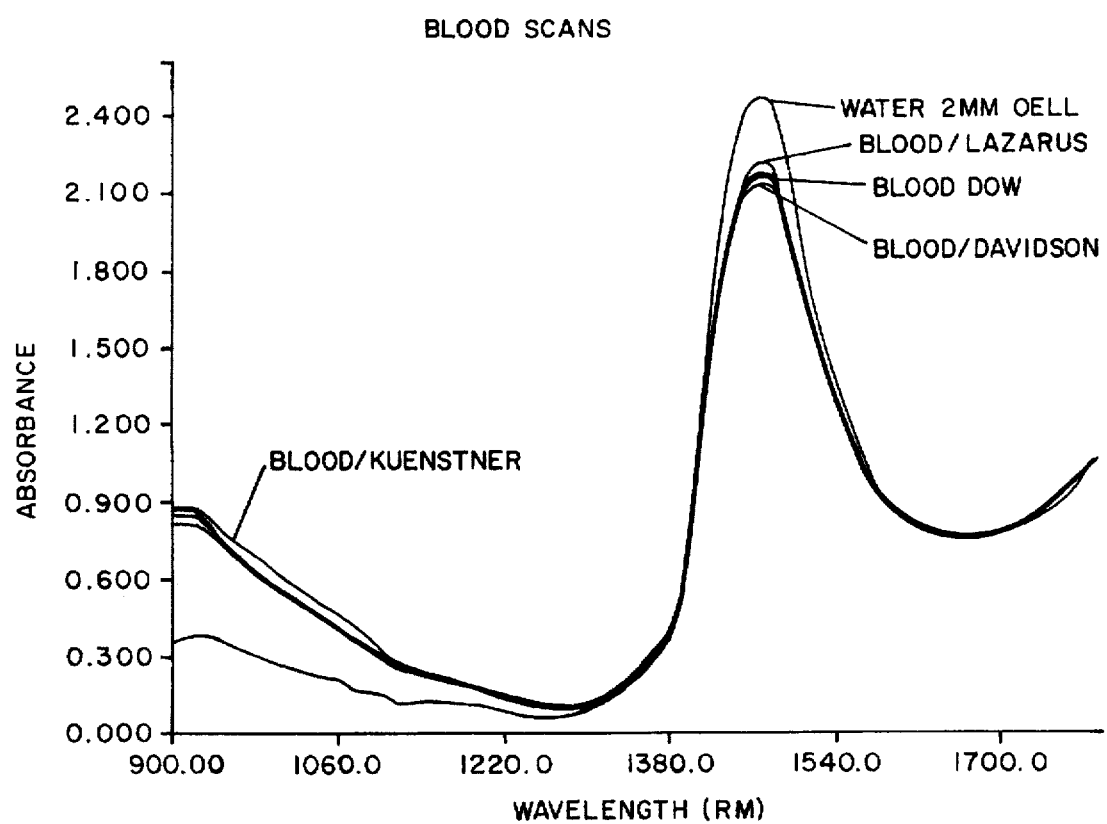
FIG. 3 shows transmittance spectra of blood from 4 subjects and of water in the near-infrared region.

FIG. 3 shows transmittance spectra of blood from 4 subjects as well as a spectrum of water for comparison purposes. To obtain these spectra, samples of lysed blood were used and a cell of constant path-length of 2.0 mm was used. With the cells lysed and in the absence of scattering particles such as lipids, the differences in absorption are primarily due to chemical composition. Note the close resemblance of the blood spectra to that of water in the region from 1250 to 1380 nm. In this region, the spectra of lysed blood are similar to that of water.

A blood sample with a low hemoglobin content will have a low absorbance at 815 nm and will also have a lower absorbance at 1288 nm than a sample with normal hemoglobin content, since there is less hemoglobin absorbance at 1288 nm. Thus, a difference in absorbance between 815 nm and 1288 nm will change from subject to subject proportionately less than the absorbance at 815 nm alone. Hence the dA term is a better reference term than absorbance at a single wavelength such as 815 nm.

Figure 4:
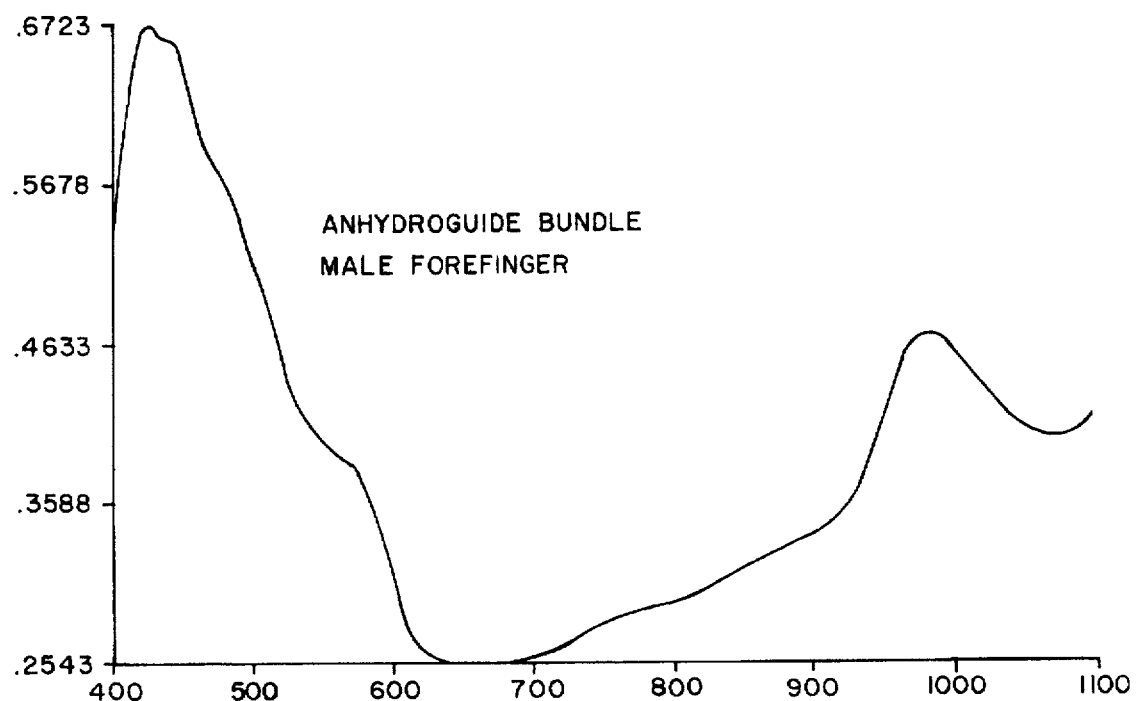
FIG. 4 shows a reflectance spectrum of the hand of this researcher in the visible and short-wavelength near-infrared regions.

FIG. 4 shows a reflectance spectrum of my hand in the visible and the short-wavelength near-infrared regions. It is evident that a significant quantity of light penetrates tissue in the region above 500 nm.

As will be realized by those of ordinary skill in the art from the foregoing description, the method of the present invention presents a simple procedure for in-vitro and in-vivo determination of the concentration of the various hemoglobin species in the blood.

As set forth above, the methods of the present invention utilize reference data to correlate the absorbance data obtained from the capillary bed tissue (in-vivo), or blood sample (in-vitro) to the concentration of the analyte being measured. Generation of suitable reference data is well within the skill of those of ordinary skill in the art. In general, reference data may be gathered, and a reference curve, or the like, generated by performing the method of the present invention on blood samples having known concentrations of the analyte to be measured. The data obtained by the method of the present invention may then be directly correlated to a known concentration of the analyte to generate a reference curve for future use. In the in-vivo embodiment, a reference curve is preferably generated by comparing and correlating the data obtained by the method of the present invention to the concentration of the analyte obtained by a traditional invasive method to generate a reference curve. Preferably, the reference data and correlation data are stored electronically in the device utilized to generate the absorbance data and the absorbance data is immediately and directly compared to the reference data to provide the concentration of the analyte or analytes.

It should be clearly understood that the forms of the present invention herein described are illustrative only and are not intended to limit the scope of the invention.

I claim:

1. A method for the in-vivo determination of the concentration of one or more hemoglobin species comprising:
   generating an absorbance data measurement by
   measuring the absorbance of light at a plurality of wavelengths in capillary bed tissue, said plurality of wavelengths including:
   at least one analyte wavelength for a hemoglobin species;
   a first reference wavelength; and
   a second reference wavelength;
   comparing the difference in absorbance at the first and second reference wavelengths to the absorbance at the analyte wavelength to generate the absorbance data measurement;
   and comparing the absorbance data measurement to a reference curve generated by a correlation study to determine the concentration of the hemoglobin species in the tissue.

2. The method of claim 1 further comprising:
   isolating the absorbance data measurement due to arterial blood by:
   generating a peak absorbance data measurement by measuring the absorbance of light at said plurality of wavelengths in capillary bed tissue during the peak of a blood pulsation through the tissue,
   generating a trough absorbance data measurement by measuring the absorbance of the light at said plurality of wavelengths in capillary bed tissue during the trough of a blood pulsation through the tissue,
   subtracting the trough absorbance data measurement from the peak absorbance data measurement to isolate the absorbance data measurement due to arterial blood; and
   comparing the absorbance data measurement due to arterial blood to said reference data.

3. The method of claim 2 wherein said analyte wavelength corresponds to a local substantially maximum absorbance of a hemoglobin species.

4. The method of claim 3 wherein an absorbance data measurement is generated at a plurality of analyte wavelengths, and each analyte wavelength corresponds to a local substantially maximum absorbance of a hemoglobin species.

5. The method of claim 3 wherein the hemoglobin species is selected from the group consisting of: oxyhemoglobin, deoxyhemoglobin, carboxyhemoglobin, methemoglobin, and sulfhemoglobin.

6. The method of claim 4 wherein the plurality of analyte wavelengths comprises an analyte wavelength for each of oxyhemoglobin, deoxyhemoglobin, carboxyhemoglobin, methemoglobin, and sulfhemoglobin.

7. The method of claim 6 further comprising: determining total hemoglobin concentration by totaling the concentration of each hemoglobin species.

8. The method of claim 2 wherein an absorbance data measurement is generated at a plurality, n, of analyte wavelengths corresponding to a plurality, n, of hemoglobin species to be measured and said comparison includes a multivariate analysis including the solution of n equations having n variables.

9. The method of claim 8 wherein the plurality of analyte wavelengths comprises an analyte wavelength for each of oxyhemoglobin, deoxyhemoglobin, carboxyhemoglobin, methemoglobin, and sulfhemoglobin.

10. A method for the in-vivo determination of the concentration of one or more hemoglobin species, the method comprising the steps of:
    a. generating an absorbance data measurement by:
       (1) measuring the absorbance of light at a plurality of wavelengths in capillary bed tissue, said plurality of wavelengths including:
           i. at least one analyte wavelength for a hemoglobin species;
           ii. a first reference wavelength; and
           iii. a second reference wavelength;
       (2) calculating the difference in the absorbance at the first reference wavelength and the second reference wavelength to define a difference term;
       (3) utilizing ratios of the difference term and absorbance measured at said analyte wavelength to generate the absorbance data measurement; and
    b. comparing the absorbance data measurement to a reference curve generated by a correlation study to determine the concentration of the hemoglobin species in the tissue.

11. The method of claim 10, wherein the step of utilizing the ratios to generate the absorbance data measurement comprises dividing the difference term by the absorbance measured at said analyte wavelength.

12. The method of claim 10, wherein the step of utilizing the ratios to generate the absorbance data measurement comprises dividing the absorbance measured at said analyte wavelength by the difference term.

13. The method of claim 10, wherein said first and second reference wavelengths are selected from wavelengths in the near infrared region ranging from approximately 800 nm to 1300 nm.

14. The method of claim 13, wherein said first and second reference wavelengths are separated by at least 300 nm.

15. The method of claim 10, further comprising the steps of: isolating the absorbance data measurement due to arterial blood by:
    generating a peak absorbance data measurement by measuring the absorbance of light at said plurality of wavelengths in capillary bed tissue during the peak of a blood pulsation through the tissue;
    generating a trough absorbance data measurement by measuring the absorbance of the light at said plurality of wavelengths in capillary bed tissue during the trough of a blood pulsation through the tissue;
    subtracting the trough absorbance data measurement from the peak absorbance data measurement to isolate the absorbance data measurement due to arterial blood; and
    comparing the absorbance data measurement due to arterial blood to said reference data.

16. The method of claim 15, wherein said analyte wavelength corresponds to a local substantially maximum absorbance of a hemoglobin species.

17. The method of claim 16, wherein an absorbance data measurement is generated at a plurality of analyte wavelengths, and each analyte wavelength corresponds to a local substantially maximum absorbance of a hemoglobin species.

18. The method of claim 17, wherein the plurality of analyte wavelengths comprises an analyte wavelength for each of oxyhemoglobin, deoxyhemoglobin, carboxyhemoglobin, methemoglobin and sulfhemoglobin.

19. The method of claim 18, further comprising the step of: determining total hemoglobin concentration by totaling the concentration of each hemoglobin species.

20. The method of claim 16, wherein the hemoglobin species is selected from the group consisting of: oxyhemoglobin, deoxyhemoglobin, carboxyhemoglobin, methemoglobin and sulfhemoglobin.

21. The method of claim 15, wherein an absorbance data measurement is generated at a plurality, n, of analyte wavelengths corresponding to a plurality, n, of hemoglobin species to be measured and said comparison includes a multivariate analysis including the solution of n equations having n variables.

22. The method of claim 21, wherein the plurality of analyte wavelengths comprises an analyte wavelength for each of oxyhemoglobin, deoxyhemoglobin, carboxyhemoglobin, methemoglobin and sulfhemoglobin.

* * * * *